(12) United States Patent
Kwok

(10) Patent No.: US 8,163,476 B2
(45) Date of Patent: Apr. 24, 2012

(54) CUDR AS BIOMARKER FOR CANCER PROGRESSION AND THERAPEUTIC RESPONSE

(75) Inventor: Tim Tak Kwok, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 12/824,026

(22) Filed: Jun. 25, 2010

(65) Prior Publication Data

US 2010/0267045 A1 Oct. 21, 2010

Related U.S. Application Data

(62) Division of application No. 12/479,616, filed on Jun. 5, 2009, now abandoned, which is a division of application No. 11/636,286, filed on Dec. 8, 2006, now Pat. No. 7,557,204, which is a division of application No. 11/046,603, filed on Jan. 28, 2005, now abandoned.

(60) Provisional application No. 60/541,863, filed on Feb. 4, 2004.

(51) Int. Cl.
*C12Q 1/68* (2006.01)

(52) U.S. Cl. .......................................................... 435/6
(58) Field of Classification Search .................... None
See application file for complete search history.

(56) References Cited

U.S. PATENT DOCUMENTS

2006/0089493 A1* 4/2006 McLachlan et al. ......... 536/23.5

FOREIGN PATENT DOCUMENTS

WO    WO 03/083074 A2    10/2003

OTHER PUBLICATIONS

Tockman et al (Cancer Res., 1992, 52:2711s-2718s).*
Freshney (Culture of Animal Cells, A Manual of Basic Technique, Alan R. Liss, Inc., 1983, New York, p. 4).*
Dermer (Bio/Technology, 1994, 12:320).*
Zips et al. (2005, In Vivo, 19:1-7).*
Coker et al. *Ann. NY Acad. Sci*, 990:757-764 (2003).
Jinno et al. *Drug Metabolism and Disposition*. 31:398-403 (2003).
Zhongxing et al. *Cancer Res.* 65(3):967-971 (2005).
Boehringer, Mannheim Biochemicals, (1994) Catalog, p. 93.

* cited by examiner

*Primary Examiner* — Laura B Goddard
(74) *Attorney, Agent, or Firm* — Knobbe Martens Olson & Bear LLP

(57) ABSTRACT

Disclosed is a novel human gene designated CUDR. Provides is also a CUDR gene as a biomarker in the diagnosis of human cancers and a cancer therapy.

2 Claims, 7 Drawing Sheets

CUDR AS BIOMARKER FOR CANCER PROGRESSION AND THERAPEUTIC RESPONSE

CROSS REFERENCE TO RELATED APPLICATIONS

This application is a divisional of application Ser. No. 12/479,616 (abandoned), filed Jun. 5, 2009, which is a divisional of application Ser. No. 11/636,286, filed on Dec. 8, 2006 (U.S. Pat. No. 7,557,204), which is a divisional of application Ser. No. 11/046,603, filed on Jan. 28, 2005 (abandoned), which claims the benefit of U.S. Provisional Application Ser. No. 60/541,863 filed on Feb. 4, 2004, entitled the same, which are explicitly incorporated herein by reference in their entireties.

BACKGROUND OF THE INVENTION

1. Technical Field of the Invention

The present invention relates to a novel mammalian CUDR cDNA which encodes a cancer marker and use of CUDR gene in the diagnosis of cancer progression and therapeutic response.

2. Technical Background of the Invention

Cancer diseases account for nearly one-quarter of deaths in the United States, exceeded only by heart diseases. The disease contributes to a major financial burden to the community and to individual. In general, cancer patients often undergo chemotherapy and radiotherapy. However, the treatment outcome is not always satisfactory. There are many reasons that patients are refractory to treatment, e.g. advanced stage of cancer, development of drug resistance.

The importance of the development of a marker for early detection of cancer and the effectiveness of cancer therapeutic response is suggested. There have been many molecular tumor markers used in clinical situations. Many of these markers were found to be associated with only a small proportion of tumors, preventing their widespread use in diagnosis. Furthermore, altered expression of some of these genes has also been reported in normal cells, which leads to false-positive results. For example, prostate-specific antigen (PSA) is now used for yearly evaluations of prostate cancer in most male patients in the United States. However, about one-third of the patients with an elevated PSA were later on to show not to have a malignant form of prostate cancer. In other cases, serum carcinoembryonic antigen (CEA) levels are now used to monitor disease progression and response to therapy in patients with colorectal cancer. However, only a proportion of colorectal cancers demonstrated elevated CEA levels at the time of diagnosis. More reliable serum markers are therefore needed to improve colorectal cancer diagnosis and to follow cancer progression. For most other types of cancer, reliable molecular markers are currently not available.

In order to fully understand the pathogenesis of cancer, it will be necessary to identify novel genes that may be involved in cancer development and drug resistance. A novel CUDR gene (a 2.2 kb transcript), identified by RT-PCR based differential display, was found to be over-expressed in doxorubicin resistant tumor sublines such as human squamous carcinoma A431 and hepatocellular carcinoma HepG2 cells. Furthermore, the gene is barely detectable in human normal tissues except placenta. By comparing the expression between normal-tumor matched tissues by RT-PCR, the gene was found to overexpress predominantly in colon cancer, lung cancer, cervical cancer and estrogen receptor alpha negative breast cancer tissues. The overexpression of CUDR in tumor tissue of patients and in cells developed drug resistance indicated that the gene may act as a marker for cancer progression and also therapeutics response.

SUMMARY OF THE INVENTION

The present invention is directed towards an isolated nucleic acid encoding a polypeptide having an amino acid sequence of SEQ ID NO: 2 and the diagnosis of human cancers using the same as a biomarker.

The first aspect of the invention is directed to an isolated nucleic acid encoding a polypeptide having an amino acid sequence of SEQ ID NO: 2. Preferably, the isolated nucleic acid has a sequence of SEQ ID NO: 1.

The second aspect of the invention relates to an isolated polypeptide having an amino acid sequence of SEQ ID NO: 2.

The third aspect of the invention relates to an antibody binding specifically to the polypeptide defined herein.

The fourth aspect of the invention goes to a pharmaceutical composition for treating a tumor comprising an effective amount of an antibody defined herein, or a nucleic acid having an antisense oligonucleotide sequence of SEQ ID No: 1 or a fragment thereof, and pharmaceutically acceptable carrier, with the proviso that the tumor is not an estrogen receptor alpha positive breast cancer.

The fifth aspect of the invention is directed to a kit for diagnosing a tumor or evaluating the treatment outcome of an anticancer agent in a subject, with the proviso that the tumor is not an estrogen receptor alpha positive breast cancer, comprising:

a pair of primers for amplification or a probe for hybridization of cDNA of an nucleic acid defined herein in a biological sample from the subject; and an instructional material for use of the primers or the probe to determine the presence or the absence of the cDNA in the biological sample.

The sixth aspect of the invention is directed to a kit for diagnosing a tumor or evaluating the treatment outcome of an anticancer agent in a subject, with the proviso that the mammalian tumor is not an estrogen receptor alpha positive breast cancer, comprising:

an antibody binding specifically to the polypeptide defined herein in the biological sample from the subject; and an instructional material for use of the antibody to determine the presence or the absence of the polypeptide in the biological sample.

The seventh aspect of the invention is directed to a method for diagnosing a subject suffering from or suspected of suffering from a tumor, or for evaluating the treatment outcome of an anticancer agent in a subject suffering from a tumor, with the proviso that the tumor is not an estrogen receptor alpha positive breast cancer, comprising:

providing a biological sample from the subject; and detecting the cDNA of a nucleic acid defined herein in the sample, wherein the presence of the cDNA in the sample indicates that the subject is suffering from a tumor or has a drug resistance against the anticancer agent.

The eighth aspect of the invention is directed to a method for diagnosing a subject suffering from or suspected of suffering from a tumor, or for evaluating the treatment outcome of an anticancer agent in a subject suffering from a tumor, with the proviso that the tumor is not an estrogen receptor alpha positive breast cancer, comprising:

providing a biological sample from the subject; and detecting a polypeptide defined herein in the sample, wherein the presence of the polypeptide in the sample indicates the subject suffering from a tumor or has a drug resistance against the anticancer agent.

The ninth aspect of the invention is directed to a method for treating a tumor in a subject, comprising administrating an effective amount of an antibody, or a nucleic acid or a fragment thereof, as defined herein, to the subject, with the proviso that the tumor is not an estrogen receptor alpha positive breast cancer.

The tenth aspect of the invention is directed to a method for cloning a nucleic acid encoding a polypeptide having an amino acid sequence of SEQ ID NO: 2 or a fragment thereof in-frame into a vector comprising: amplifying a full-length cDNA of the nucleic acid by PCR; and cloning the full-length cDNA into a suitable vector.

The eleventh aspect of the invention relates to an expression vector having a nucleic acid encoding a polypeptide having an amino acid sequence of SEQ ID NO: 2. Preferably, the vector includes pcDNA-DEST40.

The twelfth of the present invention refers to an in vitro model of acquiring drug resistance in cancer cells or cell lines prepared by transfecting a nucleic acid encoding a polypeptide having an amino acid sequence of SEQ ID NO: 2 into the cells.

In the present invention, the tumor is preferably selected from the group consisting of lung cancer, hepatocellular cancer, cervical cancer, colon cancer and estrogen receptor alpha negative breast cancer.

The biological sample used in the invention is preferably selected from the group consisting of serum, plasma, and a tissue sample, but generally excludes a normal placental tissue.

Those skilled in the art should understand that in the method of the invention, the "providing a biological sample from a subject" is not a necessary feature to exploit the invention. Therefore, some embodiments of the invention may exclude this step.

DETAILED DESCRIPTION OF THE INVENTION

Figure 1:
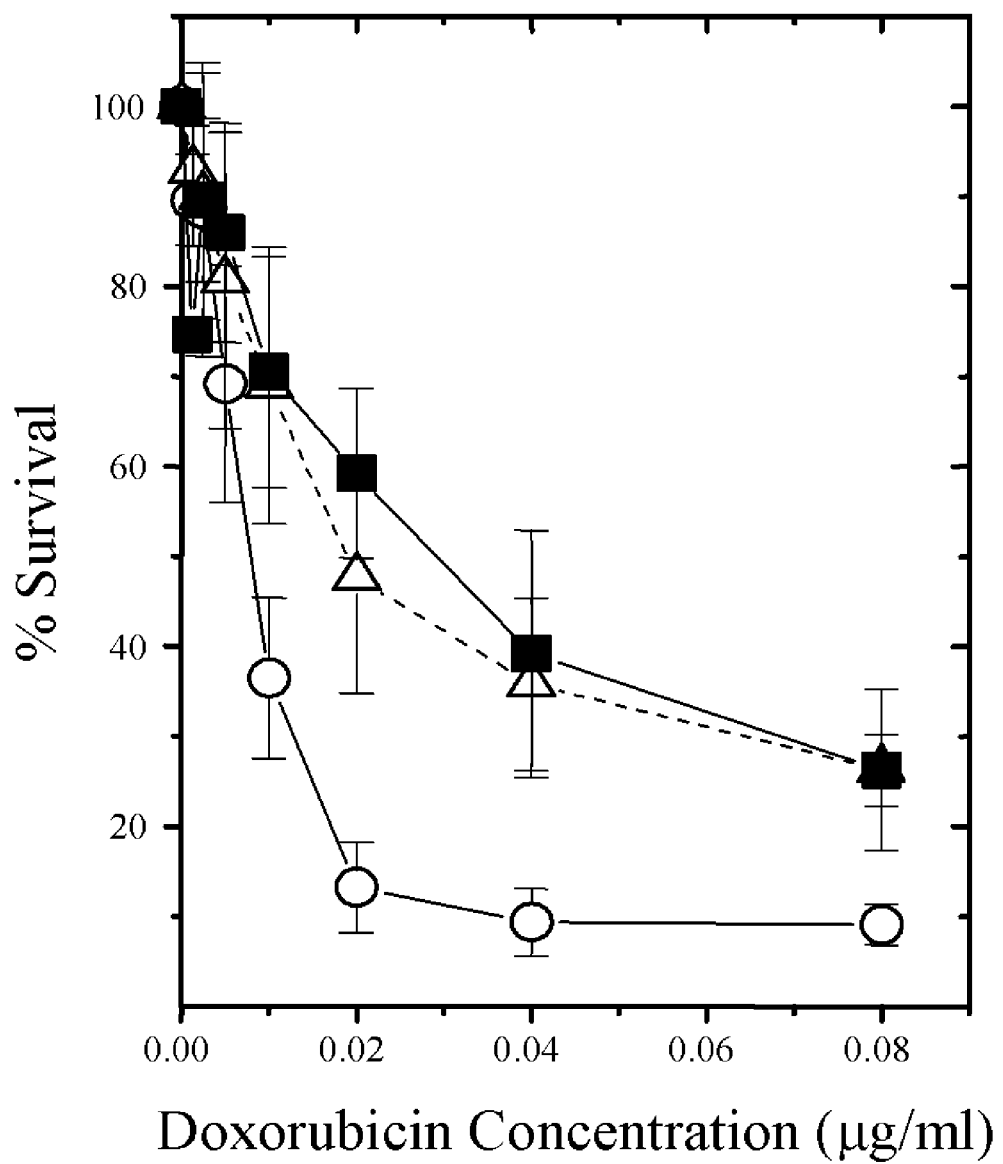
FIG. 1 shows the response of different human squamous carcinoma A431 sublines to doxorubicin as measured by MTT assay, in which open circles represent A431 parent cells; open triangles represent A5A cells and closed squares represent A10A cells.

Previous work resulted in an identification of the novel gene, designated as CUDR, of which the expression was increased in A431 cervical squamous doxorubicin-resistant subline A10A by RT-PCR based differential display (Liang et al., Cancer Res. 257:967-971). The present invention provides a new method for diagnosis of human cancer including colon, lung, cervix and breast cancer by using the CUDR.

The term "CUDR" used in the present invention means an isolated nucleic acid having a sequence of SEQ ID No:1 or a nuclei acid at least 85% (including any percentage between 85 and 100%, e.g. 90%, 95%, 100%) identical with SEQ ID NO:1 or a polypeptide encoded by the nucleic acid.

The term of "CUDR polypeptide" used herein is directed to a polypeptide having an amino acid SEQ ID NO: 2, or a sequence with an equivalent function to SEQ ID NO:2.

The term "subject" used herein refers to an animal, preferably a mammalian animal, more preferably a human.

The term "nucleic acid" used herein refers to a deoxyribonucleotide or ribonucleotide polymer in either single- or double-stranded form, and unless otherwise limited, would encompass known analogs of natural nucleotides that can function in a similar manner as naturally occurring nucleotides.

The term "primer" used herein refers to an oligonucleotide, whether natural or synthetic, capable of acting as a point of initiation of DNA synthesis under conditions in which synthesis of a primer extension product complementary to a nucleic acid strand is induced, i.e. in the presence of four different nucleoside triphosphates and an agent for polymerization (such as DNA polymerase or reverse transcriptase) in an appropriate buffer and at a suitable temperature. A primer is preferably a single-stranded oligodeoxyribonucleotide sequence.

The appropriate length of a primer depends on the intended use of the primer but typically ranges from about 15 to about 50 nucleotides. Short primer molecules generally require cooler temperatures to form sufficiently stable hybrid complexes with the template.

The term of "probe" used herein refers to an oligonucleotide which binds through complementary base pairing to a subsequence of a target nucleic acid. It will be understood by those skilled in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with digoxigenin or biotin. By assaying for the presence or absence of the probe, one can detect the presence or absence of the target.

For polymerase chain reaction (PCR), an annealing temperature of about 5° C. below Tm, is typical for stringency amplification, although annealing temperatures may vary between about 32° C. and 72° C., depending on primer length and nucleotide composition, or high stringency PCR amplification, a temperature at, or slightly (up to 5° C.) above, primer Tm is typical, although high stringency annealing temperatures can range from about 50° C. to about 72° C., and are often 72° C., depending on the primer and buffer conditions (Ahsen et al., Clin. Chem. 47: 1956-61, 2001).

The term "antibody", as used herein and if not otherwise specified, includes a polyclonal antibody, a monoclonal antibody, a chimeric antibody, a humanized antibody and a single chain antibody.

Single chain antibodies are polypeptide sequences that are capable of specifically binding a peptide or epitope, where the single chain antibody is derived from either the light or heavy chain of a monoclonal or polyclonal antibody. Single chain antibodies include polypeptides derived from humanized, chimeric or fully-human antibodies where the single chain antibody is derived from either the light or heavy chain thereof.

Preferably, polycolonal antibodies and monocolonal antibodies are used in the invention.

As used herein, an antibody or antibody fragment is referred to as "bind specifically" to a target molecule if the antibody or antibody fragment recognizes and binds the target molecule but does not substantially recognize and bind other molecules present in a sample containing target molecules.

The term of "effective amount" used herein is that amount of a composition that alone, or together with further doses, produces the desired response.

The term "carrier" denotes an organic or inorganic ingredient, natural or synthetic, with which the active ingredient is combined to facilitate the application.

The term "pharmaceutically acceptable carrier" as used herein means one or more compatible solid or liquid fillers, diluents or encapsulating substances which are suitable for administration to a subject.

The present invention discloses a full-length cDNA sequence of CUDR gene. The mRNA expression of CUDR is barely detectable in normal human tissues except placenta. The gene is proved by the invention to be overexpressed in cancer tissues such as colon, cervix, breast and lung cancer tissues compared with that in the normal tissue counterpart.

An increased expression of CUDR mRNA in hepatocellular and cervical squamous doxorubicin resistant sublines indicates the potential application of CUDR DNA or its gene product as a marker for a diagnosis or evaluating a treatment outcome of cancer therapeutic agent (also referred to herein as anticancer agent) by PCR or immunoassay.

According to the present invention, the subject that is suffering from or suspected of suffering from a cancer such as colon cancer, cervical cancer, lung cancer, breast cancer can be diagnosed by PCR or immunoassay for detecting CUDR mRNA or its gene products in a biological sample (such as serum, plasma or tissues) from the subject.

In order to detect the presence of cancer or to diagnose the cancer patients with poor prognosis in anticancer therapy, it is necessary to obtain a full-length cDNA of CUDR or an isolated polypeptide from CUDR gene. A pair of primers specific for amplification of entire CUDR cDNA is designed for polymerase chain reaction. The PCR product obtained represents the longest possible sequence and is in-frame for the translation into protein product.

The subcloning of CUDR cDNA into the Gateway entry vector facilitates a further transfer into mammalian expression vectors with an enzyme clonase for in vitro transfection and protein synthesis. Stable transfection into host cells (e.g. human cancer cells) results in an increase in CUDR expression. The V-5 epitope just downstream of the 3'-terminal of CUDR cDNA insert allows the expression by means of C-terminal fusion protein in tumor cells and facilitates an extraction of CUDR polypeptide from the cell lysate. Purification of CUDR polypeptide allows preparation of anti-CUDR antibody for diagnosis in the present invention.

Host cells and cell lines, can be prokaryotic (e.g., *E. coli*), or eukaryotic (e.g., CHO cells, COS cells, HepG2 cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples includes, hepatocellular carcinoma cells, human breast carcinoma cells, human prostate carcinoma cells, human colon carcinoma cells, human lung carcinoma cells, fibroblasts, bone marrow stem cells and embryonic stem cells.

The present invention provides a new method for treating a tumor in a subject through administrating an effective amount of a pharmaceutical composition to the subject. The composition comprises an effective amount of an antibody defined herein, or a nucleic acid having an antisense oligonucleotide sequence of SEQ ID No: 1 or a fragment thereof, and pharmaceutically acceptable carrier. The binding of antisense CUDR nucleic acids to the sense CUDR mRNA has been proved to increase the drug sensitivity of cancer cells in vitro.

When administered, the compositions of the present invention are administered in pharmaceutically acceptable preparations. Such preparations may routinely contain pharmaceutically acceptable concentrations of salt, buffering agents, preservatives, compatible carriers or excipient, supplementary immune potentiating agents such as adjuvants and alternatively other therapeutic agents, such as chemotherapeutic agents.

The pharmaceutical composition of the invention can be administered by any conventional route. The administration may, for example, be oral, intravenous, intraperitoneal, intramuscular, intracavity, subcutaneous, or transdermal.

The pharmaceutical compositions used in the foregoing methods preferably are sterile and contain an effective amount of antibody against CUDR polypeptide or antisense oligonucleotides of CUDR gene for producing the desired response in a unit of weight or volume suitable for administration to a patient. The response can, for example, be measured by detecting downstream effects such as gene expression, or by measuring the physiological effects of the CUDR composition, such as regression of a tumor, decrease of disease symptoms, modulation of apoptosis, etc.

In general, doses of antibody binding specifically to CUDR polypeptide are formulated and administered in doses between 10 ng and 300 mg, according to any standard procedure in the art. Where an antisense oligonucleotide of CUDR is employed, doses of between 1 ng and 0.1 mg generally will be formulated and administered according to standard procedures. Other protocols for the administration of the compositions herein will be known to one of ordinary skill in the art, in which the dose amount, schedule of injections, sites of injections, mode of administration (e.g., intra-tumoral) and the like vary from the foregoing.

The pharmaceutical compositions may further contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods known in the art of pharmacy. All methods include the step of bringing the active agent into association with a pharmaceutically acceptable carrier which constitutes one or more accessory ingredients. In general, the compositions are prepared by uniformly and intimately bringing the active agent into association with a liquid carrier, a finely divided solid carrier, or both, and then, if necessary, shaping the product.

Pharmaceutical compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Pharmaceutical compositions suitable for parenteral administration conveniently comprise a sterile aqueous or non-aqueous preparation antibody or antisense oligonucleotides, which is preferably isotonic with the blood of the recipient. This preparation may be formulated according to known methods using suitable dispersing or wetting agents and suspending agents. The sterile injectable preparation also may be a sterile injectable solution or suspension in a nontoxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, MACK PUBLISHING CO., EASTON, Pa.

A kit for diagnosing a tumor or evaluating the treatment outcome of an anticancer agent in a subject according to the invention generally comprises: a pair of primers for amplification or a probe for hybridization of cDNA of an nucleic acid defined herein in a biological sample; and an instructional material for use of the primers or the probe to determine the presence or the absence of the cDNA in the biological sample.

The invention also provides a kit for diagnosing a tumor or evaluating the treatment outcome of an anticancer agent in a subject comprises: an antibody defined herein in detecting a polypeptide defined herein in a biological sample from the subject; and an instructional material for use of the antibody to determine the presence or the absence of the polypeptide in the biological sample.

Biological Samples

Biological samples are obtained from subjects. Blood is commonly a sample of the invention, which can be drawn by standard methods into a collection tube, e.g., siliconized glass tube, either without anticoagulation for the preparation of serum, or with anticoagulants, e.g., EDTA, sodium citrate, or heparin for the preparation of plasma. In a preferred embodiment, fractionation of plasma or serum from whole blood is performed prior to freezing. Fractionation of fresh plasma can be done by standard methods, for example, fresh plasma or serum may be fractionated from whole blood by centrifugation according to known methods. In a preferred embodiment, centrifugation is gentle. For some embodiments of the present invention, e.g., amplification of RNA with RT-PCR, it is preferable to pretreat heparinized blood with heparinase.

Nucleic Acid Extraction from Biological Samples

Nucleic acid can be extracted from blood plasma or serum using standard extraction methods known in the art, e.g., gelatin extraction, silica, glass bead or diatom extraction, guanidine or guanidinium-based extraction, chemical extraction methods, or size exclusion or anion exchange chromatographic methods. Nucleic acid, e.g., RNA, can also be extracted using an RNAimage Kit (GenHunter Corporation, USA) according to the "blood and body fluid protocol" as recommended by the manufacturer.

Nucleic Acid Detection

After nucleic acid, e.g., RNA, has been isolated from blood plasma, serum or tissue, the nucleic acids are detected using methods known in the art. The methods of the present invention typically but not always rely on amplification or signal amplification methods for the detection of the nucleic acids. One of skill will recognize that amplification of target sequences in a sample may be accomplished by any known method, such as transcription amplification, reverse transcription PCR amplification, and self-sustained sequence replication, each of which provides sufficient amplification.

The PCR process is well known in the art. For a review of PCR methods and protocols, see, e.g., Innis, et al. eds. *PCR Protocols. A Guide to Methods and Application* (Academic Press, Inc., San Diego, Calif. 1990). PCR reagents and protocols are also available from commercial vendors, such as Roche Molecular Systems.

The nucleic acids detected can be DNA or RNA molecules. In particular embodiments of the invention, RNA molecules are detected. The first step in the amplification is the synthesis of a DNA copy (cDNA) of the region to be amplified. Reverse transcription can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described in Romero and Rotbart in Diagnostic Molecular Biology: Principles and Applications pp. 401-406, Persing et al. eds., (Mayo Foundation, Rochester, Minn. 1993) and Egger et al., *J. Clin. Microbiol.* 33: 1442-1447 (1995)).

The primers used in the methods of the invention are preferably at least about 15 nucleotides to about 50 nucleotides in length, more preferably from about 15 nucleotides to about 30 nucleotides in length.

In the present invention, the initial template for primer extension is typically first strand cDNA that has been transcribed from RNA. Reverse transcriptases suitable for synthesizing a cDNA from the RNA template are well known.

PCR is most usually carried out as an automated process with a thermostable enzyme. In this process, the temperature of the reaction mixture is cycled through a denaturing region, a primer annealing region, and an extension reaction region automatically.

The nucleic acids of the invention can also be detected using other standard techniques, well known to those of skill in the art. Although the detection step is typically preceded by an amplification step, amplification is not required in the methods of the invention. For instance, the nucleic acids can be identified by size fractionation (e.g., gel electrophoresis).

Alternatively, the target nucleic acids can be identified by sequencing according to well known techniques. Alternatively, oligonucleotide probes specific to the target nucleic acids can be used to detect the presence of specific fragments.

Sequence-specific probe hybridization is a well known method of detecting desired nucleic acids in a sample comprising cells, tissue, biological fluids and the like. Under sufficiently stringent hybridization conditions, the probes hybridize specifically only to substantially complementary sequences. The stringency of the hybridization conditions can be relaxed to tolerate varying amounts of sequence mismatch. If the target is first amplified, detection of the amplified product utilizes this sequence-specific hybridization to insure detection of only the correct amplified target, thereby decreasing the chance of a false positive.

A number of hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transitions. Examples for this assay formats are fluorescence resonance energy transfer hybridization probes, molecular beacons, molecular scorpions, and exonuclease hybridization probes (reviewed in Bustin S M. *J. Mol. Endocrin.* 25: 169-93 (2000)).

The hybridization complexes are detected according to well known techniques and are not a critical aspect of the present invention. Nucleic acid probes capable of specifically hybridizing to a target can be labeled by any one of several methods typically used to detect the presence of hybridized nucleic acids. One common method of detection is the use of autoradiography using probes labeled with $^3$H, $^{125}$I, $^{15}$S, $^{14}$C, or $^{32}$P, or the like.

Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, Tetrahedron Letts., 22 (20): 1859-1862 using an automated synthesizer, as described in Needham-VanDevanter, D. R., et al. 1984, *Nucleic Acids Res.,* 12: 6159-6168. Purification of oligonucleotides can be performed, e.g., by either native acrylamide gel electrophoresis or by anion-exchange HPLC as described in Pearson, J. D. and Regnier, F. E., 1983, *J. Chrom.,* 255: 137-149.

Polyclonal Antibodies

In order to prepare polyclonal antibodies, purified CUDR protein or polypeptide, human or non-human may be obtained.

Alternatively, all or a portion of the CUDR protein can be synthesized recombinantly in a suitable host, such as a bacterium described herein or, by expression of an appropriate DNA sequence inserted into a suitable cloning vehicle. The expression and extraction of CUDR polypeptide or protein or a portion thereof is described herein.

The expressed CUDR protein can then be purified and mixed with Freund's adjuvant (to help stimulate the antigenic response of the animal) and injected into rabbits or other appropriate laboratory animals. Following booster injections at weekly intervals, the rabbits or other laboratory animals are then bled and the sera isolated. The sera can be used directly or purified prior to use by various methods including affinity chromatography employing Protein A-Sepharose, antigen Sepharose or anti-mouse-Ig-Sepharose.

Polyclonal antibodies may also be prepared using a fragment comprising the 70 amino acid carboxy-terminal amino acid sequence, or a portion thereof as a preferred antigen. Fragments may be produced recombinantly, optionally as fusion proteins, as described herein. Such peptide antigens may be conjugated with keyhole limpet hemocyanin to improve antigenicity in vivo.

Monoclonal Antibodies

Monoclonal anti-CUDR antibodies may also be produced by conventional methods after injecting into mice purified CUDR or fragments thereof, optionally as fusion proteins, obtained as described above for preparation of polyclonal antibodies. Briefly, the purified protein or peptide is injected into mice in Freund's adjuvant, for example for nine times over a three week period. The mice spleens are removed and re-suspended in phosphate buffered saline (PBS).

The spleen cells serve as a source of lymphocytes, some of which are producing antibody of the appropriate specificity. These are then fused with a permanently growing myeloma partner cell, and the products of the fusion, hybridomas, are plated into a number of tissue culture wells in the presence of a selective agent such as HAT. The wells are then screened by ELISA to identify those containing cells making antibody specific for CUDR. These cells are then plated and after a period of growth, these wells are again screened to identify antibody-producing cells. Several cloning procedures are carried out until over 90% of the wells contain single clones which are positive for antibody production. From this procedure, a stable line of clones which produce the antibody is established. The monoclonal antibody can then be purified by affinity chromatography using Protein A Sepharose or ion-exchange chromatography, as well as variants and combinations of these techniques.

Detection of CUDR Polypeptide

Various types of immunoassay formats can be used to assay CUDR polypeptide or protein in a sample. These include sandwich ELISA, radioimmunoassay, fluoroimmunoassay, immunohistochemistry assay, dot-blot, dip-stick and Western Blot.

In a preferred embodiment, an antibody which binds specifically to CUDR polypeptide or to a fragment thereof and carries a detectable label is used and the resulting CUDR polypeptide-antibody complex is determined by measuring the detectable label, thereby determining the level of CUDR polypeptide in the sample. Alternatively, a first antibody specific for CUDR polypeptide or a fragment thereof is employed, followed by a second antibody specific for the first antibody and carrying a label which may be a directly detectable label or may be a component of a signal-generating system. Such labeled antibodies and systems are well known in the art.

Detection and determination of the label or the signal generated by the signal-generating system, compared with suitable calibration standards, permits the determination of the CUDR polypeptide-antibody complex present in the sample and hence of CUDR polypeptide.

The second antibody carries a label which may be any suitable directly detectable label or a component of any suitable signal-generating system. Many examples of these are well known from the field of immunoassay. Labeling of the second antibody with a detectable label or a component of a signal-generating system may be carried out by techniques well known in the art. Examples of labels that can be utilized to render an antibody detectable include radioisotopes, enzymes, fluorescent and chemiluminescent substances. For example, a radioactive element may be used as a directly detectable label. Exemplary radioactive labels include the γ-Emitters $^{124}$I, $^{125}$I, $^{128}$I, and a $^{131}$I. A fluorescent label may also be used as a directly detectable label. For example, suitable fluorophores include coumarin, rare earth metal ions, chelate or chelate complexes, fluorescein, rhodamine and rhodamine derivatives.

Suitable labels also include metal complexes, stable free radicals, vesicles, liposomes, colloidal particles, latex particles, spin labels, biotin/avidin and their derivatives. Enzyme-linked signal-generating systems may be used, including alkaline phosphatase, amylase, luciferase, catalase, beta-galactosidase, glucose oxidase, glucose-6-phosphate dehydrogenase, hexokinase, horseradish peroxidase, lactamase, urease and malate dehydrogenase. The activity of the enzyme can be detected by measuring absorbency, fluorescence or luminescence intensity after reacting the enzyme with an appropriate substrate. When enzymes are used as a label, the linkage between enzyme and antibody may be achieved by conventional methods such as glutaraldehyde, periodic acid and maleimide methods.

Solid matrices to act as solid supports suitable for immobilizing an antibody include microtitre plates, such as those obtainable from Falcon Plastics, Oxnard, Calif., or, for example, regular ELISA microtitre plates (Immulon II, Dynax, Chantilly, Va.) and Streptavidin-coated ELISA microtitre plates (Reacti-Bind, Pierce, Rockford, Ill.), and microtitre strips, such as those obtainable from Dynatech, Alexandria, Va.

Antibodies may be immobilized on a solid support by conventional methods which are well known in the art In accordance with a preferred embodiment of the invention, a sample of a body fluid is contacted with a first antibody which binds specifically to CUDR to form a complex, the first antibody being immobilized on a solid support. Sufficient time is allowed to permit binding of the CUDR of the sample to the immobilized antibody. The solid support is then washed and contacted with a second antibody which binds specifically to the first antibody and is labeled with a detectable label or has attached to it a signal-generating system. The label or generated signal bound to the solid support is determined, providing a measure of the complex present in the sample, and hence determining the level of CUDR in the sample.

The present invention will be further described with reference to the drawings.

EXAMPLE 1

Response of Different A431 Sublines to Doxorubicin by MTT Assay

Responses of A431 parent cells, A5A and A10A cells to doxorubicin (DOX) were compared in this Example.

A431/A5A cells were A431 cells survived from treatment with 5 µg/ml of DOX, and A10A cells were derived from A5A cells survived from treatment with 10 µg/ml of DOX.

Cells were seeded in 96-well plates for 2 days and incubated with various concentrations of DOX for 5 days. At the end of the incubation, the cells were incubated in 50 µl of a 0.1 mg/ml solution of 3-[4,5-dimethylthiaol-2-yl]-2,5-diphenyltetrazolium bromide (MTT) at 37° C. for 3 h and lysed in 150 µl of dimethyl sulfoxide at room temperature for 30 min. The absorbance of each well was measured at 580 nm in a microplate reader. The survival percentage of cells was calculated as the ratio between cells with drug treatment and cells without drug treatment.

The results averaged from 5 separated experiments were shown in FIG. 1, O: A431 parent cells; A: A431/A5A cells; and ■: A431/A10A cells. Error bar: standard deviation. As shown in the Figure, the A431/A5A cells and A10A cells were more resistant to DOX than the parent cells.

Figure 2:
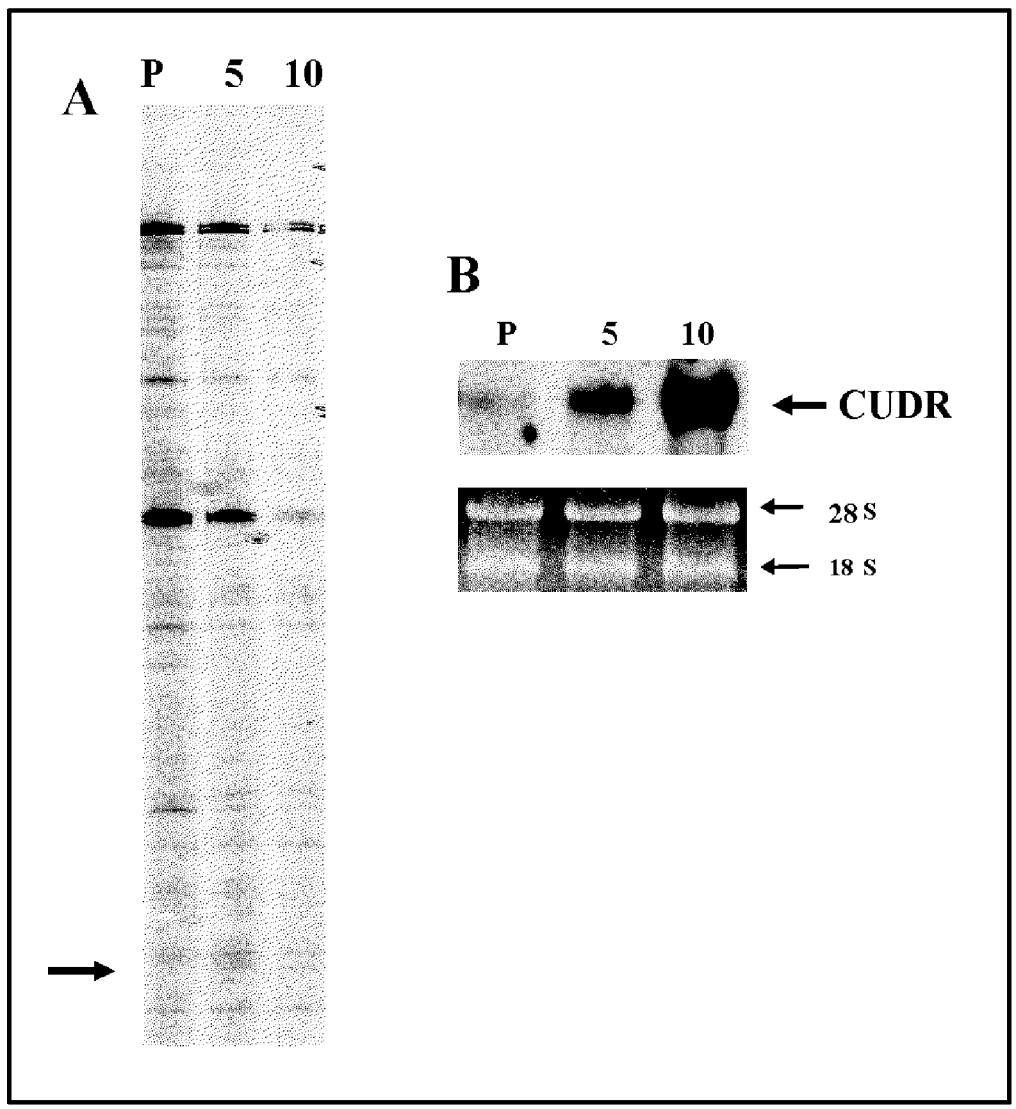
FIGS. 2A and 2B show the relative expression of CUDR (in arrow) in RT-PCR based differential display and Northern blot analysis respectively. The 18S and 28S rRNA demonstrated equal loading of total RNA in each lane. P: A431 parent cells; 5: A431/A5A cells; 10: A431/A10A cells.

Furthermore, the drug resistant cells as shown in FIG. 2 were found to over-express CUDR. This supported that CUDR over-expression induced drug resistance in cells.

EXAMPLE 2

Isolation and Identification of Target Genes

Isolation of Differentially Expressed mRNAs

The isolation of differentially expressed mRNA between A431 parent cells and drug resistant A5A and A10A cells was carried out by using the RNAimage Kit (GenHunter Corporation, USA). Briefly, 0.1 µg/µl of DNA-free RNA was reverse transcribed with MMLV reverse transcriptase, 20 µM of dNTP and one-based-anchored oligo-dT primers, followed by PCR reaction in the presence of short arbitrary primer, 2 µM of dNTP and [alpha-$^{35}$S]dATP for 40 cycles of the following parameters: 94° C. for 30 sec, 40° C. for 2 min, 72° C. for 30 sec followed by 72° C. for 5 min. RT-PCR products were resolved in 6% denaturing polyacrylamide gel until the xylene dye in the gel reached the bottom. The gel was blotted onto a 3M paper and dried under vacuum at 80° C. for 1 h. The differentially expressed cDNA pattern was visualized by autoradiography.

The results are showed in FIG. 2. The autoradiograph in FIG. 2A indicated the cDNA band corresponding to CUDR; the arbitrary primer was 5'-AAG CTT GCA CCA T-3' (SEQ ID NO:3) and the oligo-dT primer was 5'-AAG CTT TTT TTT TTT G-3' (SEQ ID NO:4). The bands identified to be differentially expressed between A431 parent cells and drug resistant cells were excised from the gel and extracted for PCR re-amplification. Subsequently, the differential expressed pattern of CUDR in A431 parent and drug resistant cells was confirmed by Northern blot analysis (FIG. 2B).

Cloning and Sequencing

The differentially expressed cDNA reamplified by PCR was subcloned into pBluescript II SK+ vector. The vector was first cut with EcoRV in the ratio as 1 µg:1 unit at 37° C. for 1 h to generate blunt ends. The linearized vector was then incubated with 2 mM dTTP in the presence of Taq DNA polymerase at 72° C. for 2 h to produce T-overhangs. The mixture was purified by phenol-chloroform extraction, precipitated with absolute ethanol and resuspended in nanopure water. Ligation of cDNA and vector DNA was carried out at 16° C. overnight with T4 DNA ligase. The molar ratio of vector to fresh PCR reamplification product in the ligation mixture was approximately 1:3 to produce recombinant DNA. Thereafter, 5 µl of ligation product was transformed into ultra-competent *E. Coli* cells and spread into LB/ampicillin plate containing 20 mg/ml X-gal and 200 mg/ml IPTG. The positive clone with DNA insert was screened by colony-PCR with the same PCR condition and parameters with that for the PCR reamplification protocol. Single colony of interest on LB plate was isolated by plasmid DNA mini-preparation kit (Qiagen, USA). The cDNA was sequenced automatically with ABI PRISM dRhodamine Terminator cycle sequencing ready reaction kit (Applied Biosystem, USA) using a pair of universal M13 vector primers. The sequence obtained was aligned with the database from Genbank using a BLAST search. The full-length cDNA of CUDR was screened and isolated by screening the human placenta arrayed cDNA library (Origene Technologies, Inc, USA). The screening procedure was performed according to the manufacturer's instructions. To identify any positive clones, a pair of primers specific for CUDR cDNA were designed according to the sequence of the cDNA band isolated from differential display, (Forward: 5'-AAT GGA CAA CAG TAC ACG C-3' (nt800) (SEQ ID NO:5); Reverse: 5'-AAG GTG CCA GTT AGC GTA T-3' (nt1247)) (SEQ ID NO:6). The positive clones were digested with NotI and the longest desired cDNA clone was identified. The full-length DNA sequences of both strands were sequenced by using library vector primers. Vector primer 3: 5'-GCAGAGCTCGIT-TAGTGAACC-3' (SEQ ID NO:7); M13 reverse 3'-CAG-GAAACAGCTATGAC-3' (SEQ ID NO:8).

It was found that the full-length CUDR gene has 2277 nucleotides (See SEQ ID NO: 1) and the protein has 123 (See SEQ ID NO: 2) amino acids.

EXAMPLE 3

Northern Blot Analysis of CUDR Expression in Different Human Cancer Cell Lines The expression of CUDR in different human cancer cell lines was examined. 10 µg of total RNA was run in each lane. Cells in exponential phase were lysed with TRI reagent (Molecular Research Center, USA). Total RNA was extracted by 1-bromo-3-chloropropane (BCP) reagent (Molecular Research Center, USA), precipitated with isopropanol and solubilized in RNase-free water. 10 µg of total RNA was run in 1% agarose/7M formaldehyde denaturing gel and blotted onto Hybond N membrane (Amersham Pharmacia Biotech, England). The cDNA probe of CUDR was obtained by PCR amplification and was resolved on 1.5% agarose gel. The cDNA was then retrieved and purified by QIAEX gel extraction kit (Qiagen, USA). The cDNA probe was labeled with Redprime II random labeling system (Amersham Pharmacia Biotech, England) by [alpha-32P]dCTP. Hybridization was performed at 65° C. for 2 h with Rapid-hyb buffer (Amersham Pharmacia Biotech, England). After stringency washes, the blot was exposed to X-ray film with intensifying screen at −80° C. Equal loading of total RNA on the gel was demonstrated by the levels of 18S and 28S of rRNA.

Figure 3:
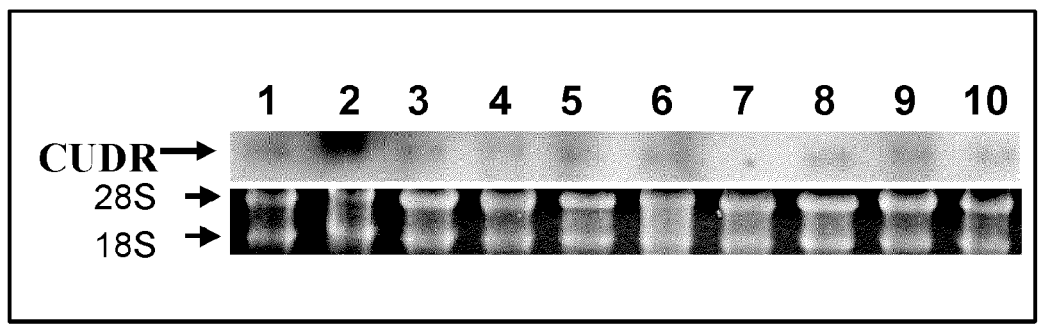
FIG. 3 shows the expression of CUDR mRNA in different cancer cell lines by Northern blot analysis.

The results shown in FIG. 3 indicate that CUDR was expressed in a wide range of human cancer cells of different tissue origin. Furthermore, the expression of CUDR was elevated in DOX resistant HepG2 cells as compared to the parent cells. The data suggested that over-expression of CUDR may induce drug resistance in HepG2 cells. In FIG. 3, Lane 1: human hepatocellular carcinoma HepG2 cells; Lane 2: doxorubicin resistant HepG2 cells; Lane 3: human hepatocellular carcinoma Hep3B cells; Lane 4: human breast carcinoma MCF-7 cells; Lane 5: human breast carcinoma MDA-468 cells; Lane 6: human cervical carcinoma HeLa cells; Lane 7: human prostate carcinoma PC-3 cells; Lane 8: human colon carcinoma HT-29 cells; Lane 9: human colon carcinoma Caco-2 cells; Lane 10: human lung carcinoma Calu-6 cells. The 18S and 28S rRNA demonstrated equal loading of total RNA in each lane.

EXAMPLE 4

Roles of CUDR in Drug Resistance

The role of CUDR in sensitivity of cells to doxorubicin was examined. Human squamous carcinoma A431 cells were transfected with either plasmid carrying the full-length CUDR cDNA or antisense oligonucleotides of CUDR. The cells were seeded in a 96-well plate for 4 h before incubation with full-length CUDR plasmid DNA for 24 h or CUDR oligonucleotides for 4 h. After transfection, the cells were incubated with DOX for 48 h. The cell survival was measured by MTT assay. Furthermore, the CUDR mRNA level after transfection was examined by Northern blot analysis.

The results for transfection with full-length CUDR plasmid DNA were showed in FIG. 4A and the results for transfection with antisense CUDR oligonucleotides were shown in FIG. 4B, respectively. In FIG. 4A, ---o--- (C): cells without transfection; -■- (CUDR): cells transfected with full length CUDR. In FIG. 4B, ---o--- (C): Cells without transfection treatment; -●- (S): transfection with sense CUDR oligonucleotides; -■- (AS): transfection with CUDR antisense oligonucleotides.

Antisense sequence for CUDR was: 5'-CAAGGTGC-CAGTTAGCGTAT-3' (nt1347-1367) (SEQ ID NO:9) and the sequence for the sense oligonucleotides was complementary to that of the antisense. The 18S and 28S rRNA in Figures demonstrated the equal loading of total RNA in each lane for Northern blot analysis.

Figure 4:
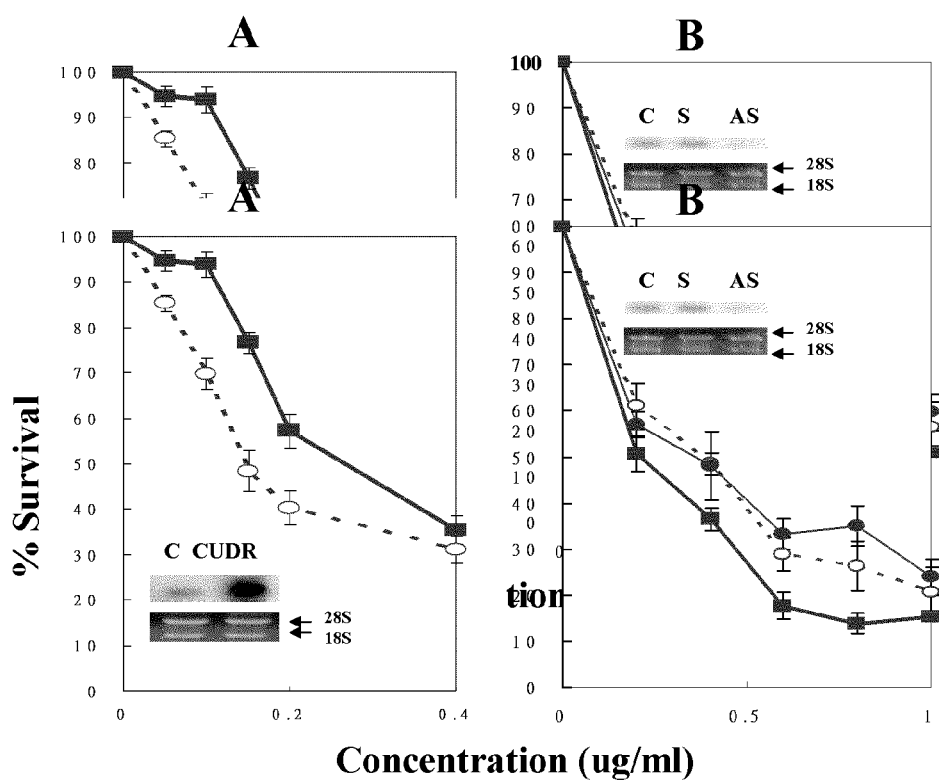
FIG. 4 shows the effect of transfection with full-length and antisense oligonucleotides of CUDR on doxorubicin sensitivity of A431 cells.

As shown in FIG. 4, transfection with full-length CUDR increased the doxorubicin resistance in A431 cells while transfection with the antisense CUDR oligonucleotides increased the DOX sensitivity of cells. The results confirmed the role of CUDR in drug resistance in cells and supported that CUDR can be used as a biomarker for therapeutic response of cancer. In addition, the results also supported that targeting the CUDR can increase drug sensitivity in cells.

EXAMPLE 5

Mechanisms of CUDR in Drug Resistance

The response of stable CUDR transfectants of human squamous carcinoma A431 cells to doxorubicin and Taxol was examined in this Example.

A431 cells were transfected with a vector carrying the full-length CUDR cDNA or an empty vector. After transfection, the cells were selected with G418 and individual colony was picked for establishment as stable transfectants. The stable transfectants were maintained in culture supplemented with G418. The response of cells to drugs was measured by both MTT assay and DNA fragmentation assay.

For the MTT assay, the cells were seeded in a 96-well plate for 2 days and incubated with various concentrations of DOX or Taxol for 5 days. At the end of the incubation, the cells were incubated with 50 µl of a 0.1 mg/ml solution of 3-[4,5-dim-ethylthiaol-2-yl]-2,5-diphenyltetrazolium bromide (MTT) at 37° C. for 3 h and lysed in 150 µl of dimethyl sulfoxide at room temperature for 30 min. The absorbance of each well was measured at 580 nm in a microplate reader. The percentage of cell survival was calculated as the ratio between cells with drug treatment and cells without drug treatment. The MTT results for DOX and Taxol were shown in FIGS. 5A and 5C respectively. ○: control cells, i.e. A431 cells transfected with empty vector; ▲: stable CUDR transfectant of A431 cells. Error bar: standard deviation. As shown in the Figures, the CUDR transfectants were more resistant to DOX and Taxol as compared to the control cells.

One of the action mechanisms for anticancer drug on human cancer cells would be apoptosis induction, in general, the higher the apoptosis induction, the more the effectiveness of the drug in killing the cancer cells. On the other hand, refractory to apoptosis induction is also believed to be one of the possible causes for cancer development.

DNA fragmentation assay, one of the common methods, was conducted to assess the apoptotic response of cells upon treatment with anticancer drug. The cells were seeded in 60 mm Petri dish for 2 days and then exposed to various concentrations of DOX or Taxol for 3 days. After incubation, the cells were lysed in lysis buffer containing Tris-HCl, SDS, EDTA and protease K and incubated at 45° C. for 2 h. After phenol/chloroform extraction, DNA was precipitated with sodium acetate and 100% ethanol. After overnight digestion with RNase A at 37° C., 40 μg of the DNA sample were separated on 1.5% EtBr staining agarose gel. The DNA fragmentation pattern was viewed with UV light box. The presence of the "DNA laddering" pattern indicates the induction of apoptosis in cells; the more extensive the laddering pattern, the more significant the apoptosis induction. The apoptotic response of cells upon treatment with DOX and Taxol was shown in FIGS. 5B and 5D respectively. AN: control cells, A431 cells transfected with an empty vector; AG: stable CUDR transfectant of A431 cells; and M: 100 bp marker.

Figure 5:
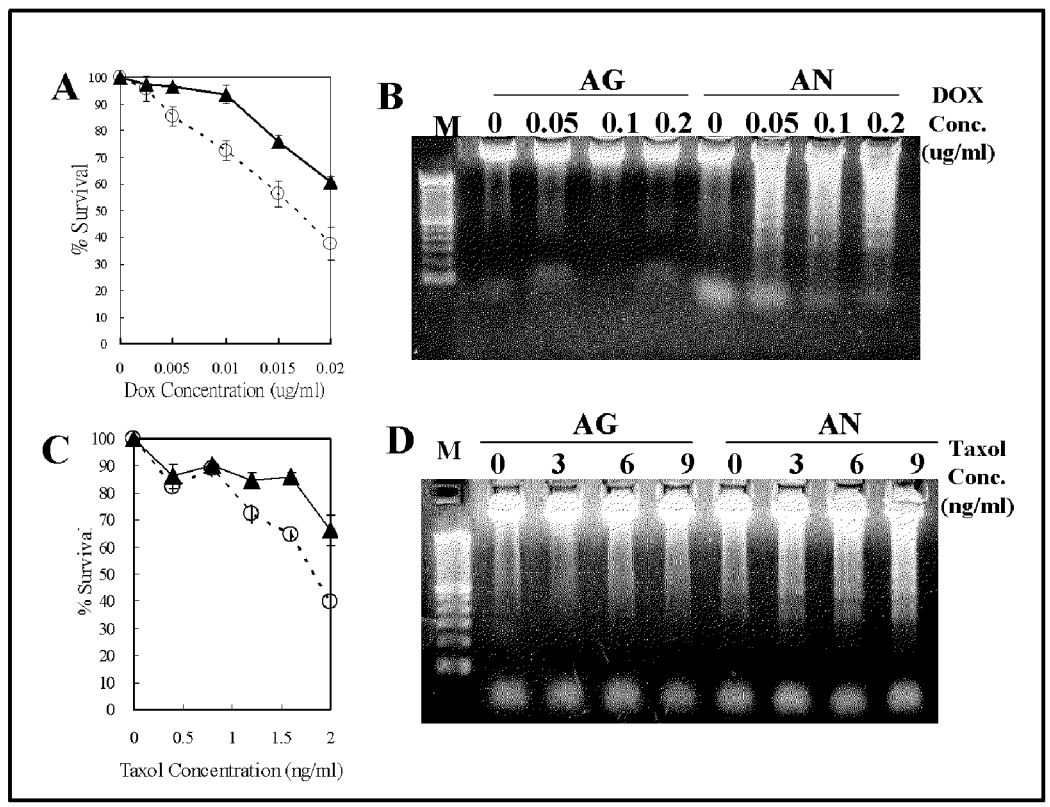
FIG. 5 shows the response of stable CUDR transfectants of human squamous carcinoma A431 cells to doxorubicin and Taxol as measured by MTT assay and DNA fragmentation assay, in which open circles or AN represent A431 cells transfected with an empty vector; closed triangles or AG represent A431 cells transfected with CUDR.

The experiments were repeated at least 3 times and the representative one was shown. As shown in FIG. 5, the CUDR transfectants were more refractory to the apoptosis induced by DOX and Taxol as compared to control cells. The results suggested that CUDR may have important role in apoptosis induction and apoptotic gene expression in cells.

In addition to the above experiments, the clonogenicity of A431 CUDR transfectants and the control cells was also examined by soft agar assay. The soft agar assay is an in vitro method for assessing the malignancy of cancer cells by growing the cells in soft agar culture. The clonogenicity of A431 CUDR transfectants was found to be >5 times greater than that of the control cells. The data therefore suggested that CUDR may increase the malignancy of cells.

EXAMPLE 6

Expression of CUDR mRNA in Different Human Tissues

Figure 6:
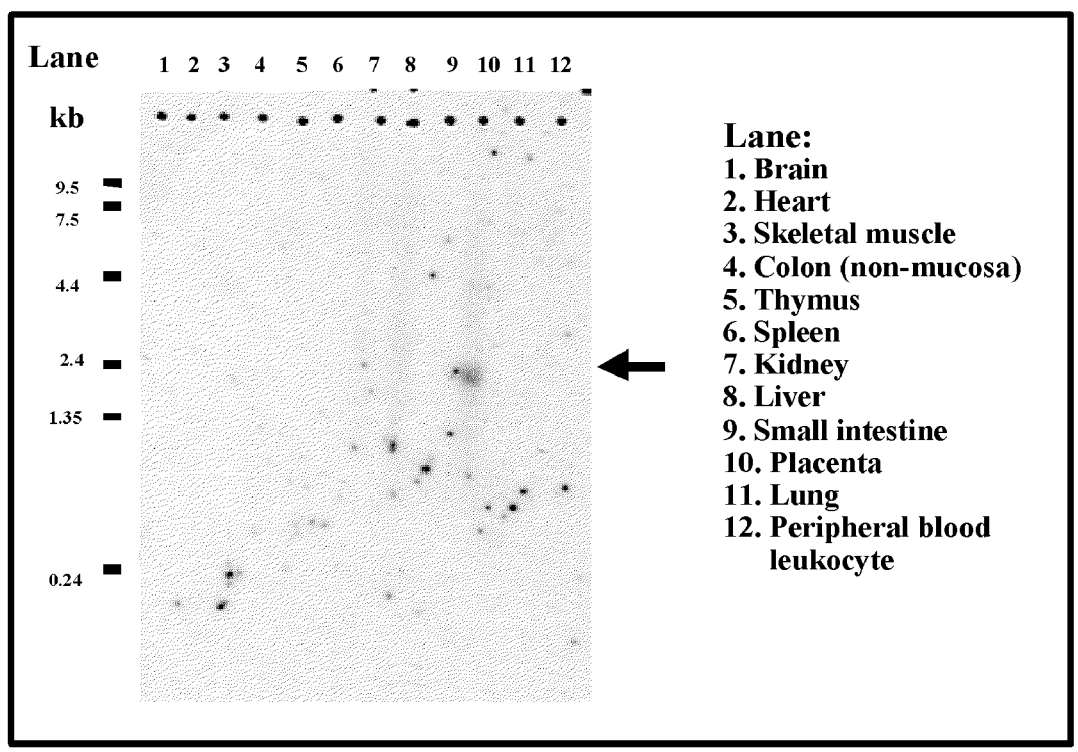
FIG. 6 shows the expression of CUDR mRNA in different human tissues by Northern blot analysis using the pre-made 12-lanes human tissue Northern (MTN) blot (ClonTech).

Northern blot analysis of the distribution of CUDR mRNA in 12 different human tissues was performed by hybridization of CUDR probe with human 12-lane Multiple Tissue Northern Blot (ClonTech, USA). As shown in FIG. 6, each lane contained 1 μg of poly-A+ RNA of 12 human tissues arranged in the order as brain, heart, skeletal muscle, colon, thymus, spleen, kidney, liver, small intestine, placenta, lung and peripheral blood leukocytes from Lane 1 to 12 respectively. The RNA integrity of the sample in each lane was confirmed by denaturing electrophoresis and equal loading was by β-actin level as done by the manufacturer. The random prime labeled CUDR was used for hybridization with the use of ExpressHyb hybridization buffer from ClonTech. Hybridization and stringency washes of the blot were performed as described by the manufacturer before exposure to X-rays film.

The results from FIG. 6 indicated that CUDR was barely detectable in all 11 human tissues while it was highly expressed in placenta. The size of the single mRNA band is approximately 2.2 kb. The amount of human tissue RNA on the blot has been normalized by human β-actin level probed by the manufacturer.

EXAMPLES 7-9

Expression of CUDR cDNA in Normal and Tumor Matched cDNA Pairs

EXAMPLE 7

Human Cervical Tissues and Human Colon Tissues 7.5 ng of first-strand cDNA from human colon and human cervical tissues were amplified with CUDR gene specific primers. The forward primer was: 5'-GCA CCC TAG ACC CGA AA-3' (SEQ ID NO:10) and the reverse primer was: 5'-GCC ACC TGG ACG GAT AT-3' (SEQ ID NO:11). There were 5 cDNA pairs for human colon tissue and one for human cervical tissue (ClonTech, USA) involved.

The cDNA samples from each pair were from the tumor and the adjacent normal tissues of an individual patient. The cDNA samples within a tissue panel were normalized to two housekeeping genes: β-actin and 23-kDa high basic protein as done by the manufacturer. PCR parameter: 94° C. for 1 min, followed by 35 cycles of 94° C. for 30 s, 58° C. for 30S, 72° C. for 30S, and then final extension 72° C. for 5 min. PCR products were resolved in 1.5% agarose gel electrophoresis.

Figure 7:
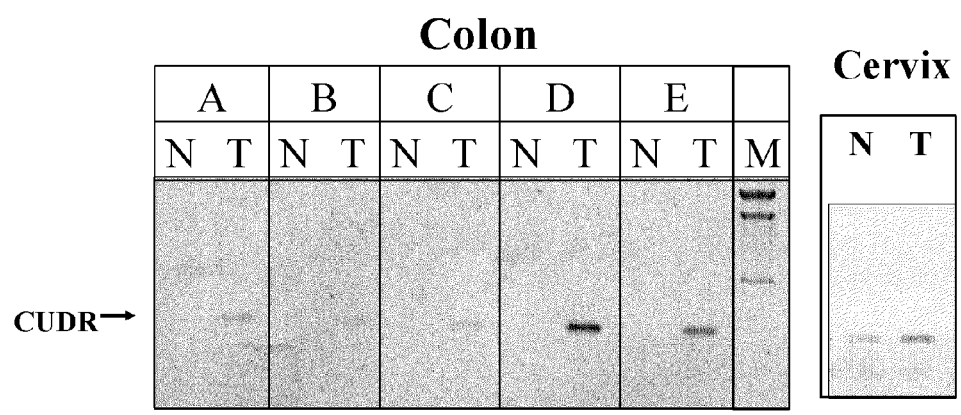
FIG. 7 shows the expression of CUDR mRNA in normal and tumor matched cDNA pairs generated from human cervical tissue and from human colon tissues from individual patients A to E.

The results shown in FIG. 7 (N: normal tissue; T: tumor tissue; and M: size marker) indicated that CUDR is up-regulated in human colon and cervical tumor tissues as compared to adjacent normal tissues. This supported the use of CUDR as a biomarker for colon and cervical cancer.

EXAMPLE 8

Human Lung Tissues 7.5 ng of first-strand cDNA from human lung tissues were amplified with CUDR gene specific primers. 5 cDNA pairs for human lung tissue (ClonTech, USA) were involved. The cDNA samples from each pair were from the tumor and the adjacent normal tissues of an individual patient. The cDNA samples within a tissue panel were normalized to two housekeeping genes: β-actin and 23-kDa high basic protein as done by the manufacturer. PCR parameter: 94° C. for 1 min, followed by 35 cycles of 94° C. for 30 s, 58° C. for 30 s, 72° C. for 30 s, and then final extension 72° C. for 5 min. PCR products were resolved in 1.5% agarose gel electrophoresis.

Figure 8:
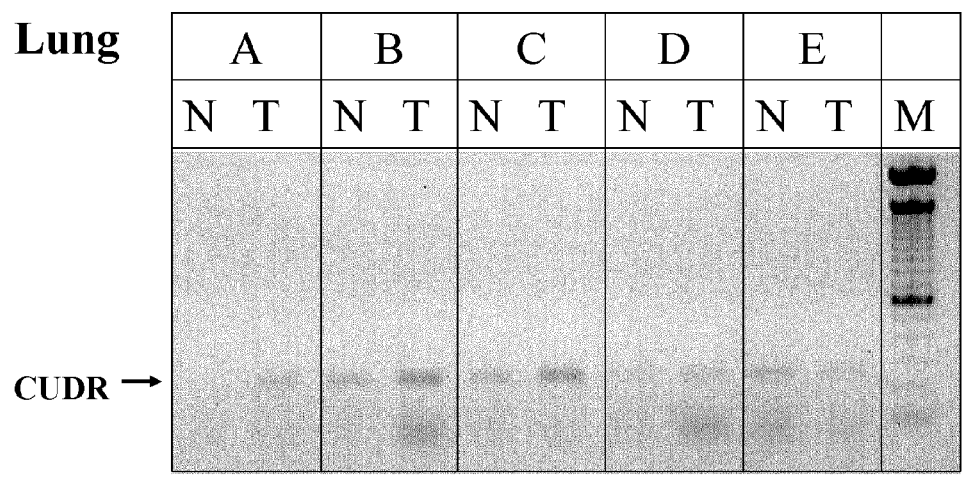
FIG. 8 shows the expression of CUDR mRNA in normal and tumor matched cDNA pairs generated from human lung tissues from individual patients A to E.

The result shown in FIG. 8 (N: normal tissue; T: tumor tissue; and M: size marker) indicated that, except for patient E, CUDR was up-regulated in human lung tumor tissues as compared to adjacent normal tissues. This supported the use of CUDR as biomarker for lung cancer.

EXAMPLE 9

Human Breast Tissues 7.5 ng of first-strand cDNA from human breast tissues were amplified with CUDR gene specific primers. There were 5 cDNA pairs for human breast tissue (ClonTech, USA) involved. The cDNA samples from each pair were from the tumor and the adjacent normal tissues of an individual patient. The cDNA samples within a tissue panel were normalized to two housekeeping genes: β-actin and 23-kDa high basic protein as done by the manufacturer. PCR parameter: 94° C. for 1 min, followed by 35 cycles of 94° C. for 30 s, 58° C. for 30 s, 72° C. for 30 s, and then final extension 72° C. for 5 min. PCR products were resolved in 1.5% agarose gel electrophoresis.

Figure 9:
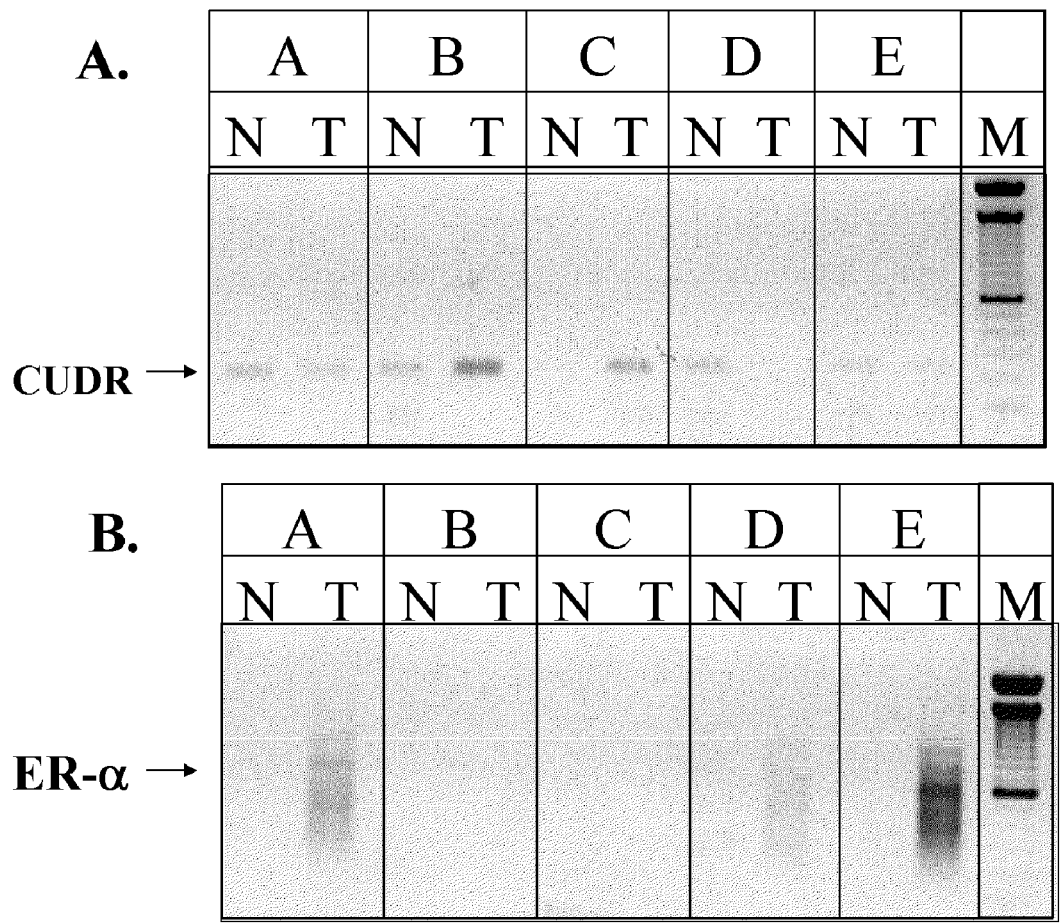
FIGS. 9A and 9B show the expression of CUDR mRNA and estrogen receptor alpha mRNA in normal and tumor matched cDNA pairs generated from human breast tissues from individual patients A to E.

The results ware showed in FIG. 9A; N: normal tissue; T: tumor tissue; and M: size marker.

Expression of Estrogen Receptor Alpha cDNA in Human Breast Tissues

Expression of estrogen receptor alpha cDNA was detected by PCR amplification using ER-α specific primers. Forward primer 5'-AGC ACC CAG TGA AGC TAC T-3' (SEQ ID NO:12); reverse primer, 5'-TGA ACC CAG TGA AGC TAC T-3' (SEQ ID NO:13). 7.5 ng of first-strand cDNA panel from human breast tissue as the same as those used for CUDR measurement were used for PCR amplification (ClonTech, USA). PCR parameter: 94° C. for 1 min, followed by 35 cycles of 94° C. for 30 s, 57° C. for 30 s, 72° C. for 30 s, and then final extension 72° C. for 5 min. PCR products were resolved by 1.5% agarose gel electrophoresis.

The result shown in FIG. 9B (N: normal tissue; T: tumor tissue; and M: size marker) indicated that the breast tumor tissues for patient A, D, and E were ERα positive while the tumor tissues for patient B and C were ERα negative. Together with the data for CUDR expression in breast tissues (FIG. 9A), the results indicated that CUDR was up-regulated in ERα negative breast tumor tissue but was down-regulated in ERα positive breast tissue. This supported the use of CUDR as biomarker for ERα negative breast tumor.

Many modifications and variations of the embodiments described herein may be made without departing from the scope, as is apparent to those skilled in the art. The specific embodiments described herein are offered by way of example only.

What is claimed is:

1. A method for diagnosing a subject suffering from or suspected of suffering from a tumor, wherein the tumor is lung cancer, comprising:

providing a pair of primers for amplification of nucleic acid, wherein said nucleic acid consists of nucleotides 1383-1636 of SEQ ID NO:1;

providing a biological sample comprising lung tissue from the subject;

detecting a cDNA comprising nucleotides 1383-1636 of SEQ ID NO:1 by amplifying nucleic acid in the sample using said primers; and diagnosing the subject as suffering from a lung tumor when the cDNA is upregulated in the biological sample as compared to cDNA in normal lung tissue.

2. The method of claim 1, wherein said pair of primers is SEQ ID NO:10 and SEQ ID NO:11.

* * * * *

SEQUENCE LISTING

```
<160> NUMBER OF SEQ ID NOS: 13

<210> SEQ ID NO 1
<211> LENGTH: 2277
<212> TYPE: DNA
<213> ORGANISM: Homo sapiens

<400> SEQUENCE: 1
agtataaagc tgcctctctc ctaactccct tcgctgactc tcttttcaga actcagccca      60
cttgcaccca agtgaattaa cagccttgtt gctcacacaa agcctgttta ggtggtcttc     120
tatacggaca tgcttgacac ttggtgccaa aatctgggcc aggggggactc cttcgtgaga    180 ccggcccct gtcctggccc tcattccgtg aagagatcca cctgcgacct cgggtcctca     240
gaccagccca aggaacatct caccaatttc aaatcggatc tcctcggctt agtggctgaa     300
gactgatgct gcccgatcgc ctcagaagcc ccttggacca tcacagatgc cgagcttcgg     360
gtaactctta cggtggagga ttcccagcca tatgaagaca ccctagctgg acgatcagtc     420
cttgtcaaaa gtctgacccc tcaaactcta cagcctcaat ggaccagacc ctacccggtc     480
atttatagca caccaactgc cgtccatctg caggaccctc tccattgggt tcaccattcc     540
agaataaagc catgcccatc agacagccag cttgatctct cctcttcctc ctggaagcca     600
caagattagg ccgagagccg atcagacaaa caacctacaa cccttaagct cctggcagcg     660
cccagccaag gccatgcttc cttgcaacac tccttccaaa tggccatccc agcatgcttc     720
caagcaggct tcatccgttc ctctggaccc tcatctctta agacctgccg cctataaaaa     780
ggattatatc ttgagaccct atcctctaaa attttttcca cacccaaaac aaaaaatctc     840
tgggtcaaaa gtctaaaacg cttaggctgg caaccatcag atccttgccc atggtgtcct     900
caagcctact ctcatgaaat ggacaacagt acacgcatat ggggccagtt ccacatattt     960
ggcaaccaga ccagcatcca ggacaacaca aagtatgttg tttgttgtta gagggcttgg    1020
gacatttcac tctttgccag cctcagctta atccaggaga caaagattat tttccttatt    1080
atctcttctg cataggatct gcaatcagaa ctattgaact tctccattca gaccgccact    1140
cacacctatg ggaaagggt aatgtatcat cggcttagca acagggaata ctattcgtat     1200
gatggaaaat ggggacaaaa ggctttggta cataaaacat tattccttcc ttggcctaaa    1260
aactcatcgc cacctacatt aaagctaata tgcctgatta ctgtttttag agaacttatt    1320
ttattagggc agttccaagc tcaaaaatac gctaactggc accttgttag ctacataaaa    1380
atgcacccta gacccgaaac ttactagact cattataaaa ttttctttaa ggtgtccacg    1440
cagtccctgg tcacacttga agcagtccgg agaaatatca gccctacccc agtaatcccc    1500
agaaggaact tacactttt tttaatcttt tcctacaact tcatatttta taaataaaaa     1560
gacaaaaatg tcaggcctgt gagctgaagc ttagccattg taacccctgt gacctgcaca    1620
tatccgtcca ggtggcctgc aggagccaag aagtctggag cagccgaaaa accacaaaga    1680
```

-continued

| | |
|---|---|
| agtgaaacag ccagttcctg ccttaactaa ttaacccacc ttacgacatt ccaccattat | 1740 |
| gacttgtcca ccattatgac ttgttcctgc cctgccccaa ctgatcaatc aaccctgtga | 1800 |
| cattcttctc ctggacaatg agtcccatca tctctccacc atgcaccttg tgacccctc | 1860 |
| ctctgctgag gataaccacc tttaactgta actttccacg cctacccaag ccctataaag | 1920 |
| ctgcccctct cctatctccc ttcactgact ctcttttcgg actcagccca cttgcaccca | 1980 |
| agtgaattaa cagccttgtt gctcacacaa agcctgattg ggtgtcttct atacggacac | 2040 |
| gcgtgacagg aacctcaacc caaaggcagt ctgatgaggt gtctaagata aaagtagcgg | 2100 |
| cacaaaggct tttgtaaaca gaggcgtttc atgtggtttt cctttccttt ccttatatgt | 2160 |
| gaaaaggtga cagaaaagaa atcttcctaa aagagtcagc cactgctgtg aaaaaaaaaa | 2220 |
| aaaaaaaaaa aaaaaaaaaa aaaaaaaaaa aaaaaaaaaa aaaaaaaaaa aaaaaaa | 2277 |

<210> SEQ ID NO 2
<211> LENGTH: 123
<212> TYPE: PRT
<213> ORGANISM: Homo sapiens

<400> SEQUENCE: 2

Met Leu Pro Cys Asn Thr Pro Ser Lys Trp Pro Ser Gln His Ala Ser
1               5                   10                  15

Lys Gln Ala Ser Ser Val Pro Leu Asp Pro His Leu Leu Arg Pro Ala
            20                  25                  30

Ala Tyr Lys Lys Asp Tyr Ile Leu Arg Pro Tyr Pro Leu Lys Phe Phe
        35                  40                  45

Pro His Pro Lys Gln Lys Ile Ser Gly Ser Lys Val Asn Ala Ala Gly
    50                  55                  60

Asn His Gln Ile Leu Ala His Gly Val Leu Lys Pro Thr Leu Met Lys
65                  70                  75                  80

Trp Thr Thr Val His Ala Tyr Gly Ala Ser Ser Thr Tyr Leu Ala Thr
                85                  90                  95

Arg Pro Ala Ser Arg Thr Thr Gln Ser Met Leu Phe Val Val Arg Gly
            100                 105                 110

Leu Gly Thr Phe His Ser Leu Pro Ala Ser Ala
        115                 120

<210> SEQ ID NO 3
<211> LENGTH: 13
<212> TYPE: DNA
<213> ORGANISM: Artificial Sequence
<220> FEATURE:
<223> OTHER INFORMATION: Arbitrary primer

<400> SEQUENCE: 3
aagcttgcac cat                                                      13

<210> SEQ ID NO 4
<211> LENGTH: 16
<212> TYPE: DNA
<213> ORGANISM: Artificial Sequence
<220> FEATURE:
<223> OTHER INFORMATION: Oligo-dT primer

<400> SEQUENCE: 4
aagctttttt tttttg                                                   16

<210> SEQ ID NO 5
<211> LENGTH: 19
<212> TYPE: DNA

```
<213> ORGANISM: Artificial Sequence
<220> FEATURE:
<223> OTHER INFORMATION: Forward primer

<400> SEQUENCE: 5
aatggacaac agtacacgc                                                    19

<210> SEQ ID NO 6
<211> LENGTH: 19
<212> TYPE: DNA
<213> ORGANISM: Artificial Sequence
<220> FEATURE:
<223> OTHER INFORMATION: Reverse primer

<400> SEQUENCE: 6
aaggtgccag ttagcgtat                                                    19

<210> SEQ ID NO 7
<211> LENGTH: 21
<212> TYPE: DNA
<213> ORGANISM: Artificial Sequence
<220> FEATURE:
<223> OTHER INFORMATION: Vector primer

<400> SEQUENCE: 7
gcagagctcg tttagtgaac c                                                 21

<210> SEQ ID NO 8
<211> LENGTH: 17
<212> TYPE: DNA
<213> ORGANISM: Artificial Sequence
<220> FEATURE:
<223> OTHER INFORMATION: M13 reverse primer

<400> SEQUENCE: 8
caggaaacag ctatgac                                                      17

<210> SEQ ID NO 9
<211> LENGTH: 20
<212> TYPE: DNA
<213> ORGANISM: Artificial Sequence
<220> FEATURE:
<223> OTHER INFORMATION: Synthetically prepared oligonucleotide
      sequence

<400> SEQUENCE: 9
caaggtgcca gttagcgtat                                                   20

<210> SEQ ID NO 10
<211> LENGTH: 17
<212> TYPE: DNA
<213> ORGANISM: Artificial Sequence
<220> FEATURE:
<223> OTHER INFORMATION: Forward primer

<400> SEQUENCE: 10
gcaccctaga cccgaaa                                                      17

<210> SEQ ID NO 11
<211> LENGTH: 17
<212> TYPE: DNA
<213> ORGANISM: Artificial Sequence
<220> FEATURE:
<223> OTHER INFORMATION: Reverse primer

<400> SEQUENCE: 11
gccacctgga cggatat                                                      17
```

```
<210> SEQ ID NO 12
<211> LENGTH: 19
<212> TYPE: DNA
<213> ORGANISM: Artificial Sequence
<220> FEATURE:
<223> OTHER INFORMATION: Forward primer

<400> SEQUENCE: 12
agcacccagt gaagctact                                              19

<210> SEQ ID NO 13
<211> LENGTH: 19
<212> TYPE: DNA
<213> ORGANISM: Artificial Sequence
<220> FEATURE:
<223> OTHER INFORMATION: Reverse primer

<400> SEQUENCE: 13
tgaacccagt gaagctact                                              19
```